(12) United States Patent
Suehling et al.

(10) Patent No.: US 8,311,303 B2
(45) Date of Patent: Nov. 13, 2012

(54) METHOD AND SYSTEM FOR SEMANTICS DRIVEN IMAGE REGISTRATION

(75) Inventors: Michael Suehling, Erlangen (DE);
Martin Huber, Uttenreuth (DE);
Grzegorz Soza, Nürnberg (DE)

(73) Assignee: Siemens Corporation, Iselin, NJ (US)

( * ) Notice: Subject to any disclaimer, the term of this patent is extended or adjusted under 35 U.S.C. 154(b) by 201 days.

(21) Appl. No.: 12/986,212

(22) Filed: Jan. 7, 2011

(65) Prior Publication Data

US 2012/0014559 A1 Jan. 19, 2012

Related U.S. Application Data

(60) Provisional application No. 61/294,256, filed on Jan. 12, 2010.

(51) Int. Cl.
*G06K 9/00* (2006.01)
*A61B 6/00* (2006.01)

(52) U.S. Cl. .......................... 382/128; 382/294; 378/21

(58) Field of Classification Search ................. 382/100, 382/103, 128, 129, 130, 131, 132, 133, 134, 382/157, 168, 171, 173, 181, 189–190, 219, 382/232, 254, 274, 276, 291, 294, 305, 312; 345/419; 378/4, 21, 62
See application file for complete search history.

(56) References Cited

U.S. PATENT DOCUMENTS

| | | | | |
|---|---|---|---|---|
| 6,101,238 A * | 8/2000 | Murthy et al. | ................. | 378/62 |
| 7,855,723 B2 * | 12/2010 | Preiss et al. | ................... | 345/419 |
| 8,218,849 B2 * | 7/2012 | Lu et al. | ......................... | 382/131 |
| 2010/0080434 A1 * | 4/2010 | Seifert et al. | .................. | 382/131 |
| 2011/0002520 A1 * | 1/2011 | Suehling et al. | .............. | 382/131 |

* cited by examiner

*Primary Examiner* — Seyed Azarian (57) ABSTRACT

A method and system for automatic semantics driven registration of medical images is disclosed. Anatomic landmarks and organs are detected in a first image and a second image. Pathologies are also detected in the first image and the second image. Semantic information is automatically extracted from text-based documents associated with the first and second images, and the second image is registered to the first image based the detected anatomic landmarks, organs, and pathologies, and the extracted semantic information.

32 Claims, 4 Drawing Sheets

METHOD AND SYSTEM FOR SEMANTICS DRIVEN IMAGE REGISTRATION

This application claims the benefit of U.S. Provisional Application No. 61/294,256, filed Jan. 12, 2010, the disclosure of which is herein incorporated by reference.

BACKGROUND OF THE INVENTION

The present invention relates to registration of medical images, and more particularly, to automatic semantics driven registration of medical images of a patient.

Image registration is a crucial technique to provide comparisons of medical images of a patient. For example, image registration can be used to compare medical images of a tumor before and after some treatment is administered or for pre and post interventional (e.g., stent placements) medical image comparisons.

Some state of the art workstations provide tools and algorithms for rigid image alignment (i.e., translation and rotation). However, due to the elastic nature of the human body, the limited degrees of freedom may not be sufficient to ensure that corresponding anatomical structures in different medical images are well-aligned to each other. A variety of elastic image registration techniques have recently been proposed. In such techniques, a number of image similarity measures are typically used together with various optimization algorithms to attempt to ensure that corresponding structures in the medical images are matched to each other. Typically, these approaches utilize a regularization term that imposes some smoothness on the deformation field to make the problem less ill-posed. The resulting deformation field is therefore a compromise between attention to detail and numerical stability and divergence. One shortcoming of such global regularization is that regions of specific interest in the medical images are not treated differently from other areas that are not of interest. In addition, changes of the image data, such as changes due to interventions (e.g., stent placement) or partial organ resections, are typically not handles well by such conventional image registration techniques.

BRIEF SUMMARY OF THE INVENTION

The present invention provides a method and system for automatic semantic driven registration of medical images. Embodiments of the present invention provide a semantics drive image registration framework that can be applied to 2D and 3D image data from various imaging modalities, including magnetic resonance (MR), computed tomography (CT), ultrasound, X-ray, etc. In various embodiments of the present invention, knowledge about anatomy, pathology, and imaging protocol parameters, such as contrast bolus phase, can be extracted from images by automatic parsing and semantic labeling. Clinical Context information can be obtained by semantic parsing of text-based data, such as Radiology Information System (RIS) information, clinical reports, or other DICOM header information. Additional clinical context information may be derived from user interactions during image reading. All extracted knowledge can be used to tune the registration focus to situation-specific diagnostic needs to ensure that anatomical structures of a particular diagnostic interest are aligned as precisely as possible.

In one embodiment of the present invention, anatomic landmarks and organs are detected in a first image and a second image. Semantic information is automatically extracted from at least one text-based document associated with at least one of the first and second images. The second image is registered to the first image based at least in part on the detected anatomic landmarks and organs and the extracted semantic information. Pathologies can also be detected in the first and second images, and the second image can be registered to the first image based at least in part on the detected anatomic landmarks, organs, and pathologies, and the extracted semantic information.

These and other advantages of the invention will be apparent to those of ordinary skill in the art by reference to the following detailed description and the accompanying drawings.

DETAILED DESCRIPTION

The present invention is directed to a method and system for automatic semantics driven registration of medical images, such as computed tomography (CT), magnetic resonance (MR) images, ultrasound images, X-ray images, etc. Embodiments of the present invention are described herein to give a visual understanding of the image registration method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Figure 1:
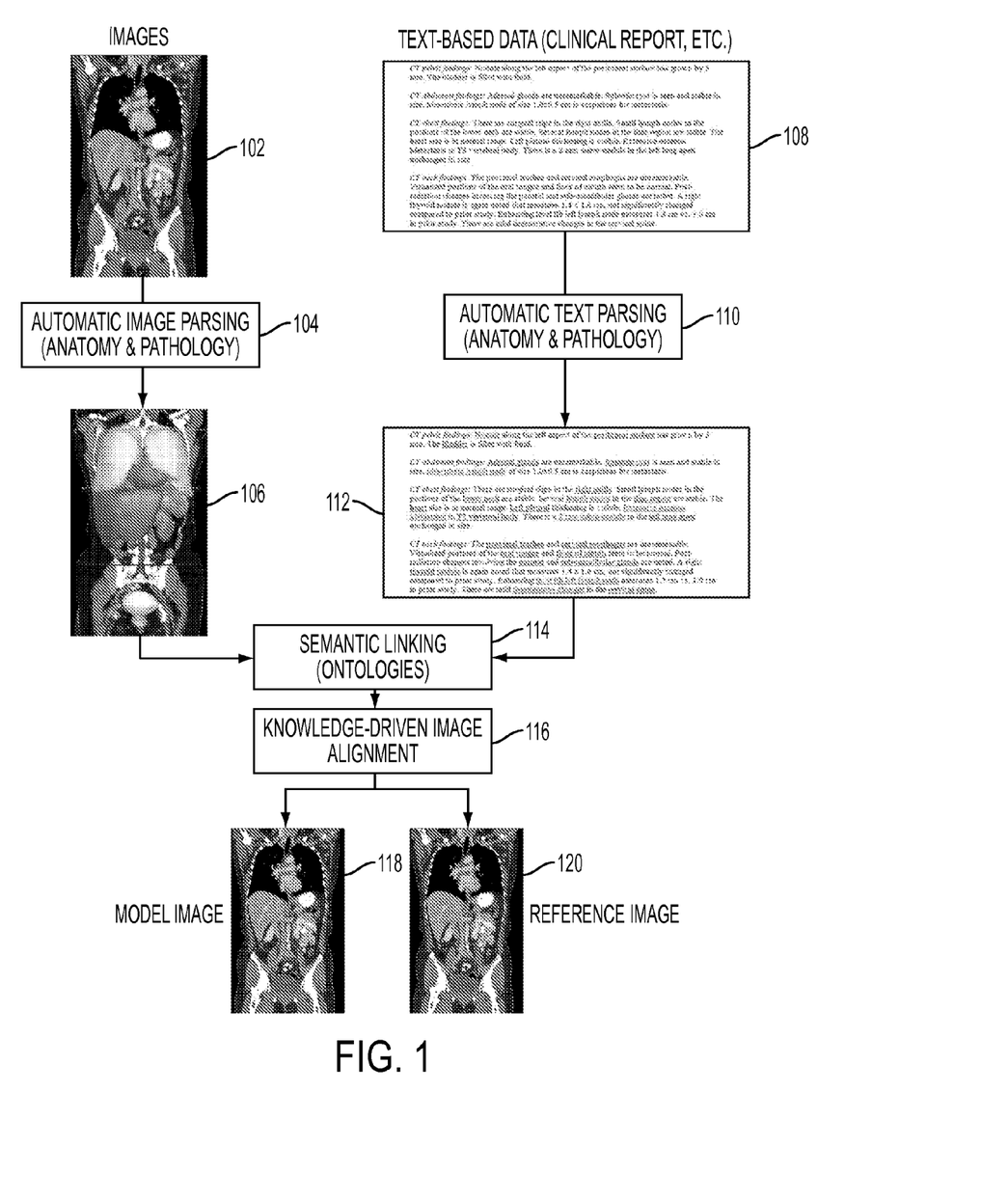
FIG. 1 illustrates the semantics driven image registration framework according to an embodiment of the present invention.

Embodiments of the present invention are directed a semantics driven image registration framework that can be applied to 2D and 3D medical image data acquired using different imaging modalities, such as MR, CT, ultrasound, X-ray, etc. FIG. 1 illustrates the semantics driven image registration framework according to an embodiment of the present invention. Referring to FIG. 1, knowledge about anatomy, pathologies, and imaging protocol parameters, such as contrast bolus phase, is extracted from images 102 by automatic image parsing and semantic labeling at block 104. For example, the automatic image parsing for the anatomy and pathology is used to obtain parsed image data 106. Clinical contextual information 112 is obtained by semantic parsing of text-based data 108, such as radiology information system (RIS) information, clinical reports (narrative or DICOM Structured Reports (DICOM SR)), or other image DICOM header information using automatic text parsing of the text-based data 108 for both anatomy and pathology at block 110. Additional clinical context information may also be derived from user interactions during image reading, such as switches to structure-specific windowing settings (e.g., lung windowing), performing measurements in a given image area, or eye focusing on a given image area during reading (e.g., using information obtained by an eye tracking system).

The clinical context information 112 can be correlated with the parsed image data 106 using ontology based semantic linking at block 114. At block 116, a model image 118 is registered to a reference image 120 using knowledge-driven image alignment. In this step, all extracted knowledge is used to tune the registration focus to situation specific diagnostic needs to ensure that structures of a given diagnostic interest are aligned as precisely as possible. Additional details regarding the framework of FIG. 1 are described below with reference to FIG. 2.

An advantageous aspect of the above-described semantics driven image registration framework is that is provides situation-specific alignment that is optimized for a given diagnostic need. This approach provides fully-automatic grouping of image datasets into sets of corresponding anatomical regions and contrast phases such that corresponding data can be aligned during an automatic pre-processing step before a user begins reading the case. Since the fully-elastic image registration has a high computational complexity and sometimes has too many degrees of freedom that make it prone to undesired misalignments and divergence, embodiments of the present invention ensure that image structures of given diagnostic interest are aligned more precisely using transformation models with optimal degrees of freedom and model parameters. Embodiments of the present invention may render elastic registration approaches more robust and accurate by enforcing the precise alignment of identified anchor landmark pairs and segmented and labeled organs and structures. Rather than keeping a fixed, pre-computed image alignment, embodiments of the present invention may "interpret" user interactions (e.g., change of windowing settings or eye focus) and optimize the image alignment to situation-specific needs.

Figure 2:
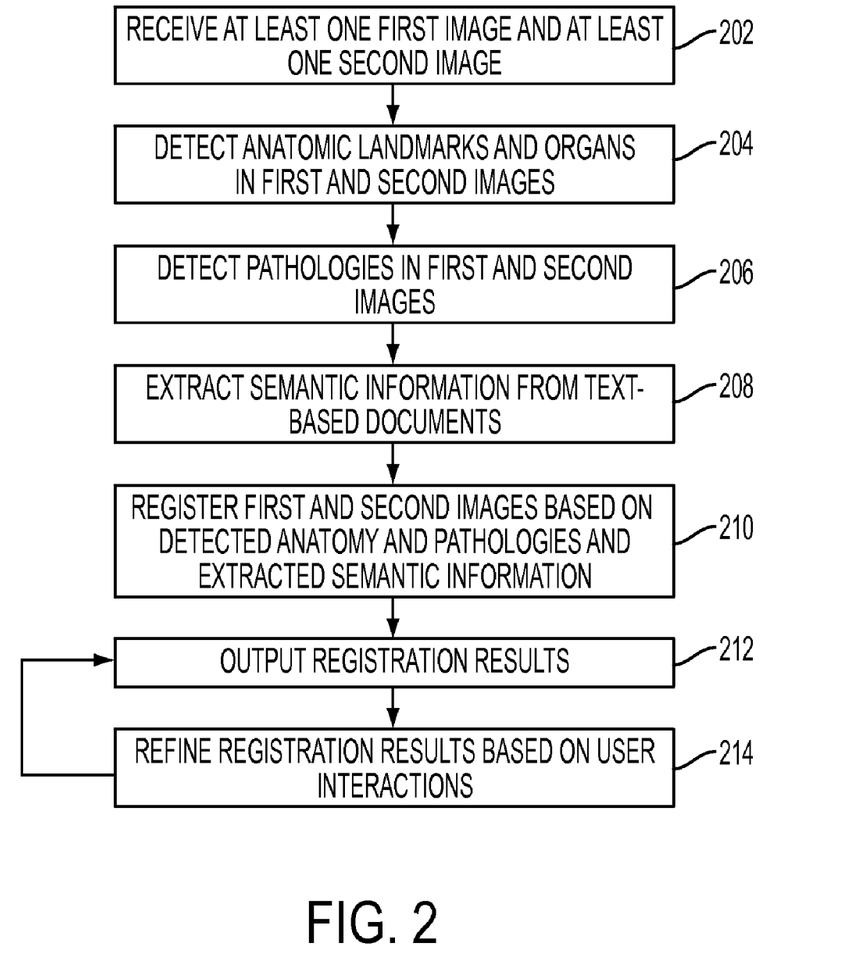
FIG. 2 illustrates a method for automatic semantics driven medical image registration according to an embodiment of the present invention.

FIG. 2 illustrates a method for automatic semantics driven medical image registration according to an embodiment of the present invention. The method of FIG. 2 transforms medical image data representing the anatomy of a patient to register two or more medical images of a patient to each other. Referring to FIG. 2, at step 202, at least one first image and at least one second image are received. The first and second images can be 2D or 3D medical images generated using any type of medical imaging modality, such as MR, CT, X-ray, ultrasound, etc. The medical images can be received directly from an image acquisition device (e.g., MR scanner, CT scanner, etc.) or can be received by loading a medical image that was previously stored, for example on a memory or storage of a computer system or a computer readable medium. In one embodiment the first image is a stored previously acquired reference image and the second image is a newly acquired model image received from an image acquisition device. The at least one first image may include a plurality of reference scans acquired at different contrast phases in order to register a second image with the reference scan having the most similar contrast phase.

At step 204, anatomic landmarks and organs are detected independently in to the first image and the second image. In particular, automatic image parsing is used to detect and label anatomic structures, including anatomic landmarks and organs in the first and second images. For example, anatomic landmarks and organs can be detected in the first and second images using the method described in United States Published Patent Application No. 2010/0080434, which is incorporated herein by reference. In such a hierarchical parsing method, one or more predetermined slices of a 3D medical image can be detected. A plurality of anatomic landmarks and organ centers can then be detected in the image using a discriminative anatomical network, where each landmark and organ center is detected in a portion of the image constrained by at least one of the detected slices. A plurality of organs, such as heart, liver, kidneys, spleen, bladder, and prostate, can then be detected as a bounding box and segmented in the image, where the detection of each organ bounding box is constrained by the detected organ centers and anatomic landmarks. The organ segmentation can be performed via a database-guided segmentation method.

The hierarchical parsing method can be used to automatically detect and label various anatomic structures including, but not limited to body landmarks, including: bones, such as the sternum, hip bones, knees, etc.; airways, such as the tracheal bifurcation (carina); and organs, such as the lung tips, liver dome and liver lobe tips, and kidney center; and vascular landmarks, such as vessel bifurcations (e.g., iliac and renal arteries); portal vein; and aortic arch.

Each anatomical landmark $x_i$ is associated with a detection confidence scored that expresses the confidence of the detection to be a true positive. Beyond landmarks (positions in space), bounding boxes and organ segmentations, such as for the liver, lungs, etc., are detected automatically. All anatomical structures can be labeled based on existing ontologies, such as the Foundational Model of Anatomy (FMA).

Furthermore, based on the detected anatomical landmarks, the contrast phase can be automatically determined for each of the first and second images. For example, in order to detect the contrast phase, a local volume of interest can be estimated at each of the detected plurality of anatomic landmarks and features can be extracted from each local volume of interest. The contrast phase of the 3D volume can then be determined based on the extracted features using a trained classifier. This method of automatically determining a contrast phase is described in greater detail in Unite States Published Patent Application No. 2011/0002520, which is incorporated herein by reference.

At step 206, pathologies are detected in the first and second images. In particular, after parsing normal anatomical structures in the first and second images in step 204, pathology landmarks are detected. For example, the detected pathologies may include, but are not limited t: lesions, such as lung lesions, liver lesions, lymph nodes, and bone lesions; and vascular abnormalities, such as calcifications, aneurysms, and thrombi. The pathologies may be detected in the first and second images using the integrated approach for lesion detection described in U.S. patent application Ser. No. 12/831,392, filed Jul. 7, 2010 and entitled "Method and System for Database-Guided Lesion Detection", which is incorporated herein by reference. In this method, search regions are defined in the 3D medical image based on the detected anatomical landmarks, organs, and bone structures. Lesions are then detected in each search region using a trained region-specific lesion detector. This method returns the position and bounding box of lesions, which may then also be used to trigger automatic lesion segmentation. Each pathology landmark $x_i$ is associated with a detection confidence score $\sigma_i$ that expresses the confidence of the detection to be a true positive. All extracted pathologies are labeled based on existing ontologies, such as the International Classification of Diseases (ICD-10).

At step 208, semantic information is extracted from text-based documents associated with the first and second images. Semantic information corresponding to the detected anatomy and pathologies in the first and second images can be extracted from text-based documents, such as Radiology Information System (RIS) information, such as the requested procedure, clinical reports (e.g., narrative or DICOM Structure Reports (SR)), or other DICOM header information, associated with the images. Information obtained from such text-based documents, such as the requested procedure in the RIS, conveys important information about the diagnostic interest of structures in the image data. Examples of requested procedures include "Bone lesion follow-up" or "Liver lesion follow-up". The semantic parsing is also applied to requests of automatic image pre-processing (e.g., detection of lung nodules by a CAD algorithm) that is sent along with the image data. Information about the contrast bolus and phase (e.g., native, arterial, venous) applied can also be extracted, for example, from DICOM header tags (Series Description, Image Comments), if available.

The knowledge extraction is realized by a fully automatic search and mapping of formal concepts using existing ontologies, such as the FMA and ICD-10 ontologies. Identified semantic concepts in clinical reports can be highlighted and displayed as a hyperlink.

At step 210, the first and second images are registered based on detected anatomy and pathologies and the extracted semantic information. Let $f_M$ denote the model image (second image) and $f_r$ denote the reference image (first image) to which $f_M$ is transformed. The transformed model image is denoted by $f_M(g(x))$ where $g(x)$ is the model transformation to be estimated. Various types of transformation models may include a rigid transformation model (translation t and rotation matrix R), i.e., $g(x)=Rx+t$; an affine transformation model (translation t; rotation, scaling, and shear matrix A), i.e., $g(x)=Ax+t$; and elastic deformation models such as thin-plate splines. The choice of the transformation model used depends on case-specific clinical requirements. The computation of elastic registration models is typically very time consuming and not feasible in many clinical application scenarios for which large waiting times are not acceptable. In addition, elastic registration models that have too many degrees of freedom lead to the undesirable effect that non-corresponding structures in the images are mapped to each other. Therefore, linear transformation models or smooth elastic deformation models are typically applied as a compromise between attention to detail, numerical stability, and speed.

Various similarity measurements $E_D$ can be used to evaluate differences between the transformed model image $f_M$ and the reference image $f_r$. One such similarity measure is the sum of squared differences, which can be expressed as:

$$E_D = \sum_{x_k \in f_r} (f_M(g(x_k)) - f_r(x_k))^2$$

where the summation is taken over all pixels $x_k$ that belong to the overlap of the reference image and the transformed model image. The landmark information detected in the images can be incorporated by tying each pair of corresponding anatomical landmark points to each other, for example using the concept of virtual springs. This may be performed by augmenting the data term $E_D$ with a term $E_S$, corresponding to the potential energy of the springs, and minimizing the sum:

$$E = E_D + E_S$$

where the spring term is:

$$E_S = \sum_{i=1}^{S} \alpha_i \|g(x_i) - z_i\|^2.$$

S denotes the number of springs (corresponding landmark pairs), $\alpha_i$ denotes the weighting factor corresponding to each spring's stiffness, and $x_i$ and $z_i$ are the landmark positions in the model and reference image, respectively. In conventional image registration, the weighting factors $\alpha_i$ are typically chosen manually to equal a fixed constant.

According to an embodiment of the present invention, the above described image registration formulation can be automatically tuned to situation-specific needs by incorporating the extracted semantic knowledge. The extracted semantic information from the image data (i.e., the detected anatomical landmarks, organs, and pathologies) can be used to automatically identify subsets of image data that cover corresponding body regions, e.g., head scans from multiple time points are assigned to one body region group and thorax scans in another group, etc. In addition, datasets belonging to corresponding contrast phases can be grouped together. This prevents non-corresponding data in the images from being aligned to each other. Anatomical landmarks can also be used for quick initialization of the image alignment. According to an advantageous embodiment, image regions of specific diagnostic interest are aligned more precisely than others given the number of degrees of freedom of a transformation model. By matching the semantic concepts obtained from automatic image parsing (steps 204 and 206) and the text-based data, such as RIS requested procedure and clinical reports (step 208), the influence of regions of interest can be increases by introducing weights $w_k$ into the data term $E_D$ as follows:

$$E_D = \sum_{x_k \in f_r} w_k (f_M(g(x_k)) - f_r(x_k))^2.$$

For example, high weights can be assigned to bone structure regions for a requested procedure, such as "Bone lesion follow up". In the case of a "Liver lesion follow-up", the automatically segmented liver regions will get higher weights than other regions such as bones. Weights $w_k$ can be normalized across the whole image dataset or a sub-region to which a given transformation model is applied. It can be noted that the example of SSD similarity measure is used above, but the present invention is not limited to any particular type of similarity measure and any pixel-based similarity measure can be used.

In addition to introducing weights into the data term $E_D$, precise alignment of corresponding landmark pairs that are of specific diagnostic interest can be enforced. In particular, weighting factors $\alpha_i$, in the term $E_S$, can be selected according to the specific diagnostic relevance of the related structures. Structures identified in the clinical reports and RIS information parsing will automatically be assigned higher weights $\alpha_i$ than others. In addition, the weight $\alpha_i$ can also be weighted by the detection confidence score i.e., $\alpha_i = \alpha_i * \sigma_i$, to account for the confidence of the automatic structure detection. Detections with high confidence $\sigma_i$ will have a higher impact than detections with lower confidence. In the case of ambiguities in finding corresponding landmark pairs (e.g., in cases of several neighboring lesions in model and reference datasets), an optimization scheme will choose the pairing-configuration that minimizes the overall cost function $E = E_D + E_S$.

The schematic information can also be used to apply appropriate transformation models and optimal degrees of freedom for different anatomical regions identified in the image. If, for example, the diagnostic focus is on bone structures, a piecewise rigid transformation model may be applied. For soft tissue regions, such as the liver, an elastic transformation model may be applied.

The actual organ segmentations may also be used to render the image alignment more accurate. This may be achieved by incorporating shape matching alignment terms into the cost function E. Such shape matching alignment terms ensure that the shapes/surfaces of corresponding segmented structures are well aligned.

At step 212, the registration results are output. For example, the registration results can be displayed on a display of a computer system. It is also possible that the registration results can be stored on a memory or storage of a computer system or on a computer readable medium. According to an advantageous implementation, the registration results can be displayed by displaying the registered images and also displaying a relevant portion of the text-based documents, such as clinical reports with the relevant portion highlighted as a hyperlink.

At step 214, the registration is automatically refined based on user interactions with the output registration results. In particular, when a user reads the output registration results, the registration is adapted based on the user interaction. If a user changes the windowing settings corresponding to a particular anatomic structure, the registration is re-calculated (as described in step 210) with an increased focus on the corresponding anatomic structure. For example, if the user switches to lung windowing settings during reading of CT data, the image alignment focus is shifted to the automatically identified lung region in the images and the potentially identified lesions in the lung. The registration is similarly refocused when the user switches to windowing settings for other structures, such as the liver, brain, soft-tissue, or bone. When a user performs labeling (e.g. setting of markers) or measurements (e.g., distance or angle measurements) in a given image region, that image region is weighted more heavily in the image registration.

Further, as described above, identified semantic concepts can be highlighted as hyperlinks in the parsed clinical reports displayed with the registered images. If the user selects an identified semantic concept in the parsed clinical report, the image registration focus is shifted to the corresponding region. For example, if the user clicks on a "bladder" hyperlink in the parsed clinical reports, the images are re-registered with increased weight on the bladder region.

According to another embodiment of the present invention, additional user input may be obtained without the knowledge of the user. For example, during reading of the displayed images, eyes of the user may be tracked with an eye tracking system, and the areas of the image can be weighted based on the amount of time the eyes of the user have spent focusing on each image area. The image registration can then be weighted using the eye-tracking based weights.

As illustrated in FIG. 2, after the refinement of the registration in step 214, the method returns to step 212 and outputs the refined registration results. The method may then continually refine the registration results based on ongoing user interactions.

It is to be understood that the semantics driven image registration described herein is not restricted to the specific similarity measure $E_D$ and spring term $E_S$ described exemplarily above, but is also applicable to other similarity terms as well. In addition, embodiments of the present invention apply to all transformation models g(x) (rigid, affine, and elastic). The semantics driven image registration method is also not restricted to the registration of only two image datasets, but can also be applied to align multiple image datasets, e.g., multiple follow-up scans across time.

Figure 3:
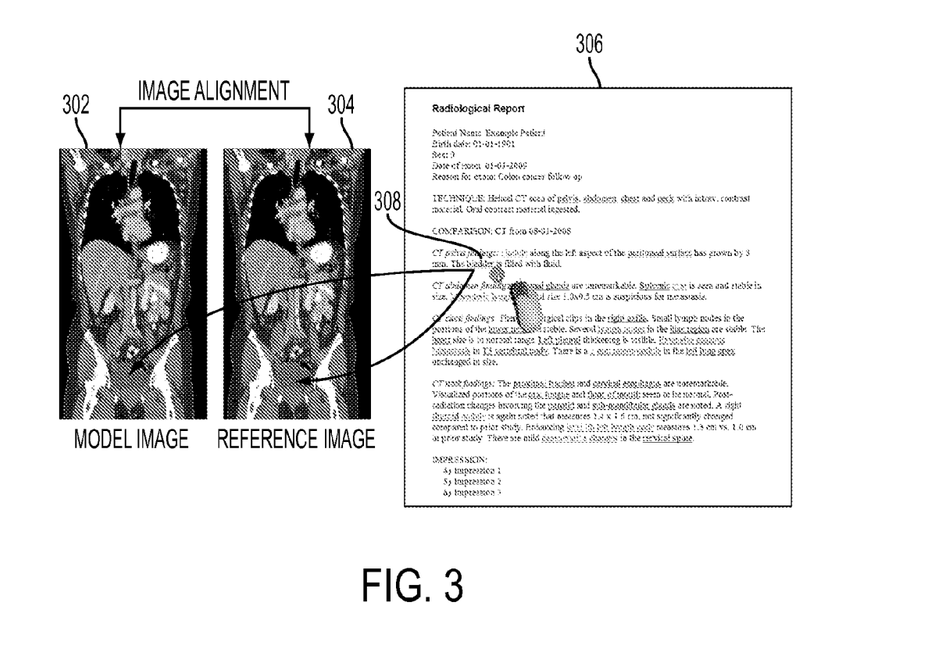
FIG. 3 illustrates exemplary registration results refined based on user interaction.

FIG. 3 illustrates exemplary registration results refined based on user interaction. As shown in FIG. 3, image registration (alignment) results are shown for a model image 302 and a reference image. In addition to displaying the aligned images 302 and 304, a parsed clinical report 306 is also displayed. In response to a user selection of a "bladder" hyperlink 308 in the parsed clinical report 306, the focus of the alignment is automatically set to the bladder in images 302 and 304, which is the area of user-interest.

Figure 4:
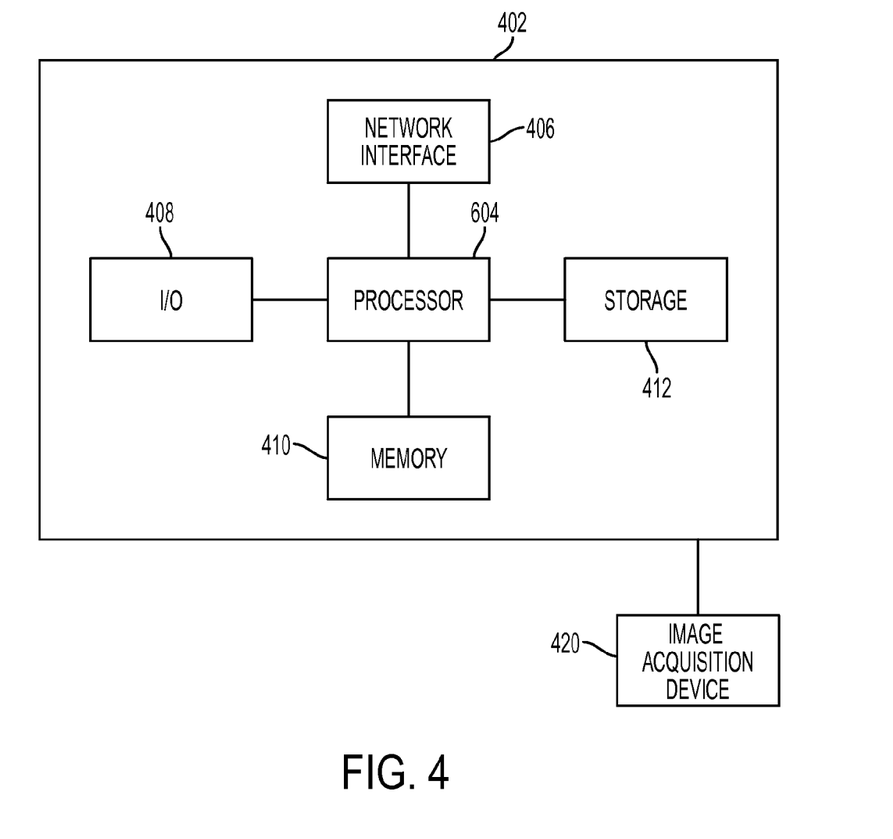
FIG. 4 is a high level block diagram of a computer capable of implementing the present invention.

The above-described methods for semantic driven registration of medical images may be implemented on a computer using well-known computer processors, memory units, storage devices, computer software, and other components. A high level block diagram of such a computer is illustrated in FIG. 4. Computer 402 contains a processor 404 which controls the overall operation of the computer 402 by executing computer program instructions which define such operations. The computer program instructions may be stored in a storage device 412, or other computer readable medium (e.g., magnetic disk, CD ROM, etc.) and loaded into memory 410 when execution of the computer program instructions is desired. Thus, the steps of the method of FIGS. 1 and 2 may be defined by the computer program instructions stored in the memory 410 and/or storage 412 and controlled by the processor 404 executing the computer program instructions. An image acquisition device 420, such as an MR scanning device or a CT scanning device, can be connected to the computer 402 to input medical images to the computer 402. It is possible to implement the image acquisition device 420 and the computer 402 as one device. It is also possible that the image acquisition device 420 and the computer 402 communicate wirelessly through a network. The computer 402 also includes one or more network interfaces 406 for communicating with other devices via a network. The computer 402 also includes other input/output devices 408 that enable user interaction with the computer 402 (e.g., display, keyboard, mouse, speakers, buttons, etc.). One skilled in the art will recognize that an implementation of an actual computer could contain other components as well, and that FIG. 4 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for automatic semantic driven registration of medical images, comprising:
    detecting anatomic landmarks and organs in a first image and a second image;
    automatically extracting semantic information from at least one text-based document associated with at least one of the first and second images by mapping the semantic information found in the at least one text-based document to a predetermined ontology; and
    registering the second image to the first image based at least in part on the detected anatomic landmarks and organs and the extracted semantic information.

2. The method of claim 1, further comprising:
detecting pathologies in the first image and the second image.

3. The method of claim 2, wherein the step of registering the second image to the first image based at least in part on the detected anatomic landmarks and organs and the extracted semantic information comprises:
registering the second image to the first image based at least in part on the detected anatomic landmarks and organs, the detected pathologies, and the extracted semantic information.

4. The method of claim 1, wherein the step of automatically extracting semantic information from at least one text-based document associated with at least one of the first and second images comprises:
automatically searching the at least one text-based document for semantic information; and
mapping semantic information found in the at least one text-based document to a predetermined ontology.

5. The method of claim 1, wherein the at least one text-based document comprises at least one of Radiology Information System (RIS) data, clinical reports, and DICOM header information.

6. The method of claim 1, wherein the step of registering the second image to the first image based at least in part on the detected anatomic landmarks and organs and the extracted semantic information comprises:
identifying a region of diagnostic interest in the first and second images based on the extracted semantic information; and
enforcing a greater precision on the registration of pixels of the first and second images in the identified region of diagnostic interest than pixels not in the identified region of diagnostic interest.

7. The method of claim 6, wherein the step of enforcing a greater precision on the registration of pixels of the first and second images in the identified region of diagnostic interest than pixels not in the identified region of diagnostic interest comprises:
increasing a weight of a similarity measure for pixels within the identified region of diagnostic interest.

8. The method of claim 1, wherein the step of registering the second image to the first image based at least in part on the detected anatomic landmarks and organs and the extracted semantic information comprises:
enforcing a greater precision on the registration of corresponding landmark pairs that are identified as structures of interest based on the extracted semantic information.

9. The method of claim 1, wherein the step of registering the second image to the first image based at least in part on the detected anatomic landmarks and organs and the extracted semantic information comprises:
identifying a region of diagnostic interest in the first and second images based on the extracted semantic information; and
automatically selecting a transformation model for transforming the second image to the first image based on the identified region of diagnostic interest.

10. The method of claim 1, further comprising:
displaying the registered first and second images; and
refining the registration of the first and second images based on user interactions with the registered first and second images.

11. The method of claim 10, wherein the step of refining the registration of the first and second images based on user interactions with the registered first and second images comprises:
shifting a focus of the registration of the first and second images based on a user selection of windowing settings.

12. The method of claim 10, wherein the step of refining the registration of the first and second images based on user interactions with the registered first and second images comprises:
shifting a focus of the registration of the first and second images based on a user performing at least one of labeling or measurements in a particular image area.

13. The method of claim 10, wherein the step of refining the registration of the first and second images based on user interactions with the registered first and second images comprises:
shifting a focus of the registration of the first and second images based on a user selection of a hyperlink in a displayed parsed clinical report.

14. The method of claim 10, wherein the step of refining the registration of the first and second images based on user interactions with the registered first and second images comprises:
tracking eyes of a user viewing the registered first and second images;
and refining the registration based on the amount of time the eyes of the user have spent in different image areas.

15. An apparatus for automatic semantic driven registration of medical images, comprising:
means for detecting anatomic landmarks and organs in a first image and a second image;
means for automatically extracting semantic information from at least one text-based document associated with at least one of the first and second images by mapping the semantic information found in the at least one text-based document to a predetermined ontology; and
means for registering the second image to the first image based at least in part on the detected anatomic landmarks and organs and the extracted semantic information.

16. The apparatus of claim 15, further comprising:
means for detecting pathologies in the first image and the second image.

17. The apparatus of claim 16, wherein the means for registering the second image to the first image based at least in part on the detected anatomic landmarks and organs and the extracted semantic information comprises:
means for registering the second image to the first image based at least in part on the detected anatomic landmarks and organs, the detected pathologies, and the extracted semantic information.

18. The apparatus of claim 15, wherein the means for automatically extracting semantic information from at least one text-based document associated with at least one of the first and second images comprises:
means for automatically searching the at least one text-based document for semantic information; and
means for mapping semantic information found in the at least one text-based document to a predetermined ontology.

19. The apparatus of claim 15, wherein the means for registering the second image to the first image based at least in part on the detected anatomic landmarks and organs and the extracted semantic information comprises:
means for identifying a region of diagnostic interest in the first and second images based on the extracted semantic information; and
means for enforcing a greater precision on the registration of pixels of the first and second images in the identified region of diagnostic interest than pixels not in the identified region of diagnostic interest.

20. The apparatus of claim 19, wherein the means for enforcing a greater precision on the registration of pixels of the first and second images in the identified region of diagnostic interest than pixels not in the identified region of diagnostic interest comprises:

means for increasing a weight of a similarity measure for pixels within the identified region of diagnostic interest.

21. The apparatus of claim 15, wherein the means for registering the second image to the first image based at least in part on the detected anatomic landmarks and organs and the extracted semantic information comprises:

means for enforcing a greater precision on the registration of corresponding landmark pairs that are identified as structures of interest based on the extracted semantic information.

22. The apparatus of claim 15, wherein the means for registering the second image to the first image based at least in part on the detected anatomic landmarks and organs and the extracted semantic information comprises:

means for identifying a region of diagnostic interest in the first and second images based on the extracted semantic information; and means for automatically selecting a transformation model for transforming the second image to the first image based on the identified region of diagnostic interest.

23. The apparatus of claim 15, further comprising:

means for displaying the registered first and second images; and means for refining the registration of the first and second images based on user interactions with the registered first and second images.

24. A non-transitory computer readable medium encoded with computer executable instructions for automatic semantic driven registration of medical images, the computer executable instructions defining steps comprising:

detecting anatomic landmarks and organs in a first image and a second image;

automatically extracting semantic information from at least one text-based document associated with at least one of the first and second images by mapping the semantic information found in the at least one text-based document to a predetermined ontology; and registering the second image to the first image based at least in part on the detected anatomic landmarks and organs and the extracted semantic information.

25. The computer readable medium of claim 24, further comprising computer executable instructions defining the step of:

detecting pathologies in the first image and the second image.

26. The computer readable medium of claim 25, wherein the computer executable instructions defining the step of registering the second image to the first image based at least in part on the detected anatomic landmarks and organs and the extracted semantic information comprise computer executable instructions defining the step of:

registering the second image to the first image based at least in part on the detected anatomic landmarks and organs, the detected pathologies, and the extracted semantic information.

27. The computer readable medium of claim 24, wherein the computer executable instructions defining the step of automatically extracting semantic information from at least one text-based document associated with at least one of the first and second images comprise computer executable instructions defining the steps of:

automatically searching the at least one text-based document for semantic information; and mapping semantic information found in the at least one text-based document to a predetermined ontology.

28. The computer readable medium of claim 24, wherein the computer executable instructions defining the step of registering the second image to the first image based at least in part on the detected anatomic landmarks and organs and the extracted semantic information comprise computer executable instructions defining the steps of:

identifying a region of diagnostic interest in the first and second images based on the extracted semantic information; and enforcing a greater precision on the registration of pixels of the first and second images in the identified region of diagnostic interest than pixels not in the identified region of diagnostic interest.

29. The computer readable medium of claim 28, wherein the computer executable instructions defining the step of enforcing a greater precision on the registration of pixels of the first and second images in the identified region of diagnostic interest than pixels not in the identified region of diagnostic interest comprise computer executable instructions defining the step of:

increasing a weight of a similarity measure for pixels within the identified region of diagnostic interest.

30. The computer readable medium of claim 24, wherein the computer executable instructions defining the step of registering the second image to the first image based at least in part on the detected anatomic landmarks and organs and the extracted semantic information comprise computer executable instructions defining the step of:

enforcing a greater precision on the registration of corresponding landmark pairs that are identified as structures of interest based on the extracted semantic information.

31. The computer readable medium of claim 24, wherein the computer executable instructions defining the step of registering the second image to the first image based at least in part on the detected anatomic landmarks and organs and the extracted semantic information comprise computer executable instructions defining the step of:

identifying a region of diagnostic interest in the first and second images based on the extracted semantic information; and automatically selecting a transformation model for transforming the second image to the first image based on the identified region of diagnostic interest.

32. The computer readable medium of claim 24, further comprising computer executable instructions defining the steps of:

displaying the registered first and second images; and refining the registration of the first and second images based on user interactions with the registered first and second images.

* * * * *